US00PP32261P2

(12) United States Plant Patent
Hansen

(10) Patent No.: US PP32,261 P2
(45) Date of Patent: Sep. 29, 2020

(54) ***KNIPHOFIA* PLANT NAMED 'LADY LUCK'**

(50) Latin Name: ***Kniphofia* hybrid**
Varietal Denomination: Lady Luck

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/873,022

(22) Filed: Jan. 15, 2020

(51) Int. Cl.
*A01H 5/02* (2018.01)

(52) U.S. Cl.
USPC ..... Plt./443

(58) Field of Classification Search
USPC ..... Plt./443
CPC ..... A01H 5/02
See application file for complete search history.

*Primary Examiner* — Annette H Para

(57) ABSTRACT

A new and distinct cultivar of ornamental Red Hot Poker, *Kniphofia* plant named 'Lady Luck', with long, gracefully-arching, strap-like, keeled, glaucous, gray-green foliage and numerous scapes beginning in late summer. Habit is large, densely-growing, winter-hardy and tolerant of heat. Numerous scapes with dense flowers of greenish buds that open to white and retain their color through dehiscence. The new plant is useful for landscaping as a specimen, en masse, or as a long-lasting cut flower.

1 Drawing Sheet

Botanical classification: *Kniphofia* hybrid.
Variety denomination: 'Lady Luck'.

STATEMENT REGARDING PRIOR DISCLOSURES UNDER 37 CFR 1.77(B)(6)

The first non-enabling disclosure of the claimed plant, in the form of a photograph and brief description, was made by Walters Gardens, Inc. on Feb. 1, 2019 on their website. Subsequently, on May 29, 2019, the claimed plant was displayed with a photograph and brief sales promotion on the "Walters Gardens 19-20 Catalog." Walters Gardens, Inc. sold the first plants of 'Lady Luck' on Sep. 23, 2019. Walters Gardens, Inc. obtained the new plant and all information relating thereto, from the inventor. No plants of *Kniphofia* 'Lady Luck' have been sold, in this country or anywhere in the world nor has any disclosure of the new plant been made more than one year prior the filing date of this application, and any such sale or disclosure of the new plant within one year was either derived directly or indirectly from the inventor.

BACKGROUND AND ORIGIN OF THE PLANT

The present invention relates to the new and distinct Red Hot Poker, *Kniphofia* 'Lady Luck' developed under the direction of the inventor at a wholesale perennial nursery in Zeeland, Mich., USA in the summer of 2012. The new plant was the result of a single seedling selection from a cross between 'Green Jade' (not patented) as the female or seed parent and 'Echo Mango' U.S. Plant Pat. No. 21,706 as the male or pollen parent. The cross was performed on Aug. 13, 2012. The plant passed initial evaluation in the summer of 2014 and was subsequently given the breeder code 12-17-1 prior to naming. *Kniphofia* 'Lady Luck' has been successfully asexually propagated by division method since 2014 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Lady Luck' differs from its parent as well as all other *Kniphofia* known to the applicant. The most similar known *Kniphofia* cultivars are: 'Flash Point' U.S. Plant Pat. No. 31,282, 'Pineapple Popsicle' U.S. Plant Pat. No. 22,969, 'Percy's Pride' (not patented) and the female parent 'Green Jade'. 'Flash Point' has slightly shorter habit in maturity, the flower buds are light chartreuse-yellow, and the flowers open to a creamy white. 'Pineapple Popsicle' is much shorter in habit and the flower buds are a lighter yellow opening to creamy white. 'Green Jade' is slightly taller in habit, the flower buds are less green and the flowers open to creamy green. 'Echo Mango' is shorter in scape and foliage height, the flowers are light orange with fewer flowers per inflorescence.

*Kniphofia* 'Lady Luck' differs from these above cultivars and all cultivars known to the inventor in that it has:

1. Gracefully arching, strap-like, keeled, gray-green foliage.
2. Moderate vigor, dense habit, winter-hardy, heat tolerant, rabbit and deer tolerant, moderate-sized clumps.
3. Numerous spikes of greenish buds transitioning through chartreuse to creamy chartreuse on tall stems that open to white;
4. Flowering beginning late summer for three weeks in Michigan.

BRIEF DESCRIPTION OF THE DRAWINGS

The photographs of *Kniphofia* 'Lady Luck' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
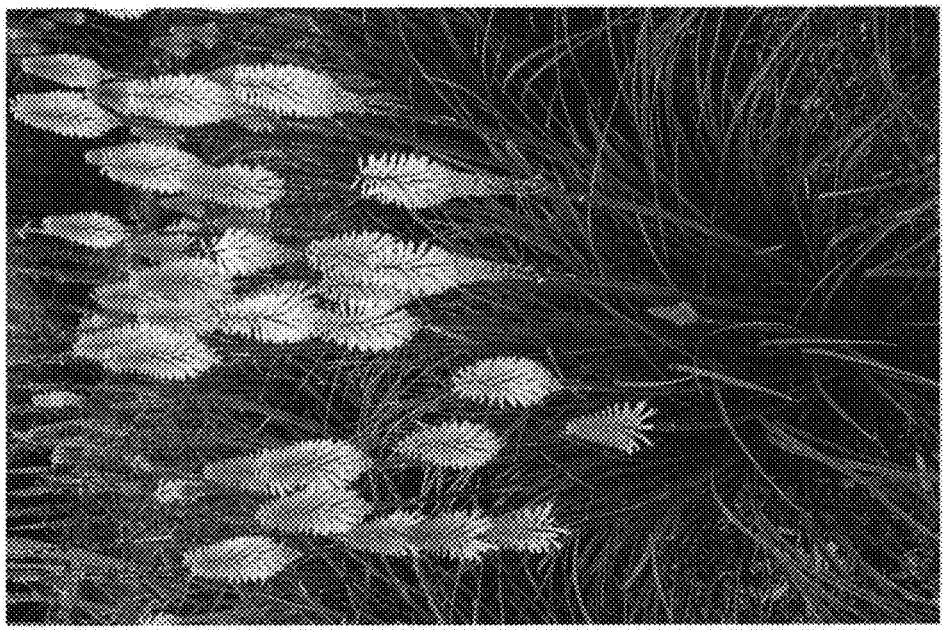
FIG. 1 shows the side-view habit of a five-year-old plant in midseason flowering.
Figure 2:
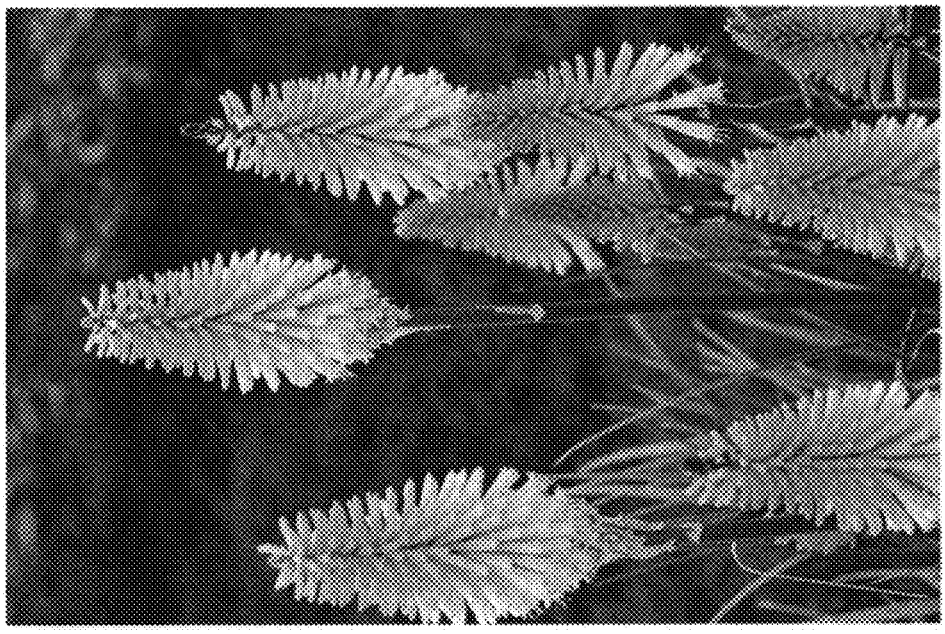
FIG. 2 shows a close-up of the flowers and buds.

The following descriptions and color references are based on the 2015 edition of The Royal Horticultural Society Colour Chart except where common dictionary terms are used. The new plant, *Kniphofia* 'Lady Luck', has not been observed under all possible environments. The phenotype may vary slightly with different environmental conditions, such as temperature, light, fertility, moisture and maturity levels, but without any change in the genotype. The following observations and size descriptions are of two-year-old and five-year-old plants in a trial garden of a wholesale perennial nursery in Zeeland, Mich. under full sun with supplemental water and fertilizer as needed.

Botanical classification: *Kniphofia* hybrid;

Parentage: *Kniphofia* 'Green Jade' as the female or seed parent and 'Echo Mango' as the male or pollen parent;

Propagation method: By garden division of the rhizome and shoot tip tissue culture;

Growth rate: Moderately vigorous, flowering in 3.5 liter containers in about 12 to 14 weeks from a 25 mm plug liner in late winter to spring and from a one-year-old bare root plant to flowering in 7 to 9 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 80.0 cm across and about 105.0 cm tall; flowering to about 110.0 cm tall; about 10 peduncles per plant;

Leaves: Linear; keeled at base, triangular in distal half; arranged up to 10 leaves per basal division; apex narrowly acute; base truncate, clasping; margin entire; no fragrance observed;

Leaf size: To about 78.0 cm long and 18.0 mm across at base, average about 62.0 cm long and 15.0 mm across at base;

Leaf color: Young base nearest RHS NN155C both abaxial and adaxial, distally between RHS N138D and RHS 189B both abaxial and adaxial; mature adaxial and abaxial nearest RHS N138D;

Leaf venation: Parallel; color same as leaf abaxial and adaxial as young and mature leaves;

Stem: Acaulescent; rhizome about 20.0 mm across at base;

Inflorescence: In spike-like raceme; cylindrical; about 250 flowers per stem; flowering portion to about 22.0 cm tall and about 8.0 cm across; lasting about three weeks; flower spacing less than 1.0 mm apart on raceme in distal region and about 2.5 cm in lowest flowers;

Peduncle: Cylindrical; glabrous; glaucous; stiff; upright; solid not fistulose; to about 110.0 cm long and 9.0 mm diameter; average 84.0 cm tall and 8.0 mm diameter; unbranched;

Peduncle color: Basal 5 cm nearest RHS 145D; proximally nearest RHS N138D, distally blend between RHS 148B and RHS 178A;

Buds one day prior to opening: Tubular with slightly swollen rounded apex and rounded base; glabrous; lustrous; about 23.0 mm long and about 3.0 mm diameter at base and 5.0 mm diameter at widest point near apex;

Bud attitude: Beginning outwardly and drooping as maturing toward anthesis;

Bud color: Seven days prior to opening nearest RHS 143C; three days prior to opening nearest RHS 145C in distal 3 mm and proximally between RHS 145D and RHS N155B; one day prior to opening nearest RHS NN155C in distal one-half and proximal one-half nearest blend between RHS 145D and RHS 150D;

Flowers: Cylindrical forming tubular corolla; perfect; incomplete; actinomorphic; individually open and effective about three to four days;

Flower size: To about 34.0 mm long to tip of exserted anthers, fused in basal about 27.0 mm; face to about 10.0 mm tall and about 11.0 mm wide; corolla tube about 5.0 mm diameter near base and about 9.0 mm near throat; corolla tube to 31.0 mm long;

Flower attitude: Drooping;

Flower fragrance: None detected;

Flowering period: Individual racemes effective for about 3 weeks; beginning late summer for about three weeks in Michigan;

Tepals: Six, in two identical sets of three; linear; both sets with acute apices and fused in basal 27.0 mm forming tube; margin entire; glabrous and lustrous abaxial and adaxial; about 31.0 mm long and about 3.5 mm across just above fusion point, about 4.0 mm long above fusion;

Tepal color (young and mature adaxial): Face and distal corolla tube nearest RHS NN155D, proximal tube between RHS NN155B and RHS 155C; (young and mature abaxial): distal corolla tube and face nearest RHS NN155D, basal one-third lighter than a blend between RHS 150D and RHS 145D;

Androecium: Six;

*Filaments*.—Six; exserted; straight; glabrous; lustrous; about 33.0 mm long and about 0.5 mm diameter; color nearest RHS NN155B.

*Anther*.—Six; ellipsoidal; dorsifixed; longitudinal; about 2.0 mm long and 1.0 mm across and 1.0 mm thick; color ventrally nearest RHS 164B.

*Pollen*.—Abundant: color nearest RHS 15A.

Gynoecium: single; about 34.0 mm long;

*Style*.—Cylindrical; straight; glabrous; lustrous; about 30.0 mm long and 0.5 mm diameter: color distally nearest RHS NN155B.

*Stigma*.—Flattened; about 0.5 mm across and tall; color nearest RHS 155C.

*Ovary*.—Superior; ellipsoidal; rounded apex, truncate base; about 3.5 mm long and 2.5 mm diameter; color nearest RHS 146D.

Pedicel: Cylindrical; glabrous; slightly glaucous; stiff; arcuate downwardly with maturity; about 3.0 mm long and about 1.0 mm diameter;

Pedicel color: Nearest RHS 147B;

Bracts: Lanceolate; at cauline nodes and subtending individual flowers; with acute apices and truncate base; to about 16.0 mm long and 8.0 mm across at base; decreasing distally; color between RHS 155D and RHS 164D;

Fruit: Tri-valved loculicidal capsule; globose to ellipsoidal; about 7.0 mm long and 6.0 mm across; glabrous; with rounded apex and rounded base; typically four to eight seeded; color as maturing nearest RHS 146A and upon maturity nearest RHS 200A;

Seed: Irregular with angular sides, acute apex and base; about 5.0 mm and 3.0 mm across; color nearest RHS 200A;

Disease and pest resistance: 'Lady Luck' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of *Kniphofia* plant named 'Lady Luck' as herein described and illustrated.

* * * * *